(12) United States Patent
Burd et al.

(10) Patent No.: US 6,456,066 B1
(45) Date of Patent: Sep. 24, 2002

(54) EDDY CURRENT PIPELINE INSPECTION DEVICE AND METHOD

(75) Inventors: John Ferris Burd, West Bridgford; James Edward Ramshaw, Cramlington, both of (GB)

(73) Assignee: Lattice Intellectual Property Limited, London (GB)

(*) Notice: Subject to any disclaimer, the term of this patent is extended or adjusted under 35 U.S.C. 154(b) by 0 days.

(21) Appl. No.: 09/486,707
(22) PCT Filed: Aug. 24, 1998
(86) PCT No.: PCT/GB98/02547
  § 371 (c)(1),
  (2), (4) Date: May 25, 2000
(87) PCT Pub. No.: WO99/13326
  PCT Pub. Date: Mar. 18, 1999

(30) Foreign Application Priority Data
  Sep. 6, 1997 (GB) .............................................. 9718891

(51) Int. Cl.[7] .............................................. G01N 27/90
(52) U.S. Cl. ........................ 324/220; 324/232; 324/242
(58) Field of Search ................................ 324/219–221, 324/232, 239–243

(56) References Cited

U.S. PATENT DOCUMENTS

| 2,790,140 A | * | 4/1957 | Bender | 324/220 |
|---|---|---|---|---|
| 4,203,069 A | * | 5/1980 | Davis | 324/220 |
| 4,292,589 A | * | 9/1981 | Bonner | 324/221 |
| 4,909,091 A | * | 3/1990 | Ellman et al. | 324/220 X |
| 5,293,119 A | * | 3/1994 | Podney | 324/242 |
| 5,532,591 A | * | 7/1996 | Logue | 324/242 |
| 5,623,203 A | * | 4/1997 | Hosohara et al. | 324/220 |
| 5,821,747 A | * | 10/1998 | Atherton et al. | 324/220 |

FOREIGN PATENT DOCUMENTS

| JP | 57-190264 | * | 11/1982 | 324/220 |
|---|---|---|---|---|
| JP | 7-248314 | * | 9/1995 | |
| JP | 8-5611 | * | 1/1996 | |

* cited by examiner

Primary Examiner—Gerard R. Strecker
(74) Attorney, Agent, or Firm—Oblon, Spivak, McClelland, Maier & Neustadt, P.C.

(57) ABSTRACT

A pipeline inspection vehicle which can be towed through a pipeline via a cable. The vehicle includes a power unit, a master processor module, and a coil which generates an eddy current field which passes along the pipe. The resultant field is detected by a master sensor ring and slave sensor ring. Information on an amplitude and phase of the detected field together with vehicle orientation information is sent to a base station which has a computer. A distance encoder also is provided to assist in locating the position of any detected faults.

20 Claims, 3 Drawing Sheets

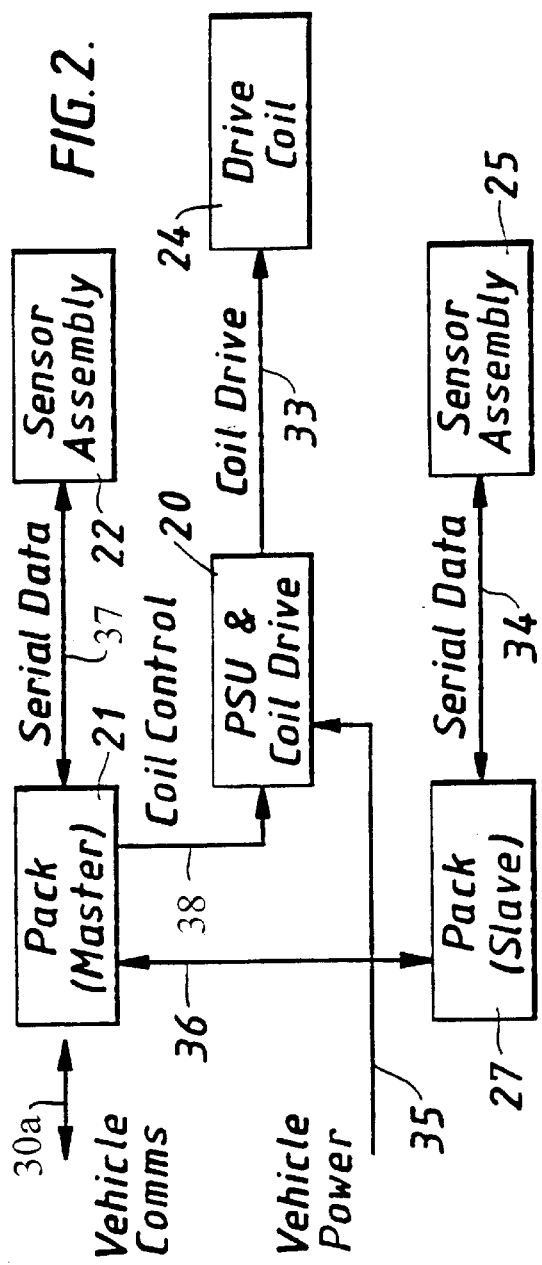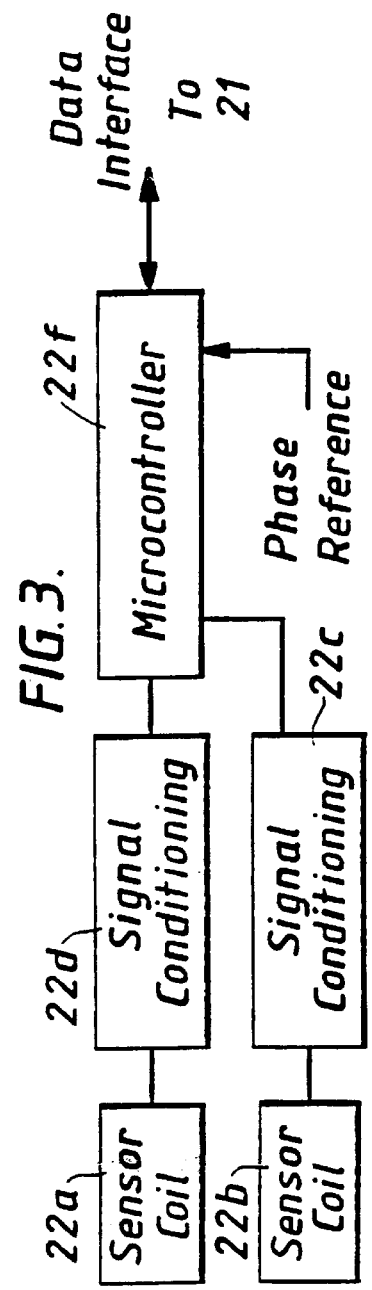

EDDY CURRENT PIPELINE INSPECTION DEVICE AND METHOD

BACKGROUND OF THE INVENTION

1. Field of the Invention

The invention relates to pipeline inspection and more specifically to a vehicle which can be towed through a pipeline to allow analysis of its wall structure.

2. Discussion of the Background

Large diameter pipes can be tested using complex pipeline pigs which may even operate when the pipes are 'live', i.e. when gas, for example, is flowing through the pipe.

In U.S. Pat. No. 4,292,589A an eddy current method and apparatus for lowering into an oil well casing is disclosed using transmitting coils and receiving pads.

In U.S. Pat. No. 4,203,069A an eddy current producing coil is shown for use with a rotor for concentrating the field.

In U.S. Pat. No. 5532591A an arrangement uses a rotating magnetic field to test flaws in the wall of a drinks can.

In EP0065325A a flaw detector uses eddy currents from a source coil with an associated detector.

In JP08005611A a flaw detector uses transmission and receiving coils utilising eddy current detection with reduced noise.

In JP03120457A an eddy current flaw detector uses coils for reducing the influence of an external baffle plate.

In JP61133856 a detector system uses both eddy currents and ultrasonic thickness measurement to aid diagnosis.

SUMMARY OF THE INVENTION

The present invention seeks to provide an improved arrangement which also allows both ferrous and non-ferrous small diameter pipes to be tested for defects.

According to the invention there is provided a pipeline inspection device for travelling through a pipeline and including generator means for generating an eddy current field within the pipeline; and detector means for detecting the resultant field and characterised in that the inspection device is configured to determine the presence of faults in both ferrous and non-ferrous pipelines, the detector means comprising first and second receivers spaced longitudinally on either side of a transmitter coil at a single location forming the generator means, said receivers being configured to receive information derived from the transmitter coil at two longitudinally spaced locations on the pipeline, said information being updated as the device travels through the pipeline and means being provided for selecting a coil excitation frequency dependent on the ferrous or non-ferrous nature of the pipeline to be tested.

Further according to the invention there is provided a method of testing a pipeline using a pipeline inspection device, said method including generating an eddy current in a coil in said device and detecting the eddy current induced in the wall of the pipeline and characterised by the steps of: selecting a coil excitation frequency dependent on the nature of the pipeline to allow both ferrous and non-ferrous pipelines to be tested, detecting the induced eddy current at two longitudinally spaced locations from the coil positioned at a single location therebetween and updating the information as the device travels along the pipeline to allow faults in the pipeline to be determined.

BRIEF DESCRIPTION OF THE DRAWINGS

The invention will now be described by way of example in which:

FIG. 2 shows the control and data handling arrangements of FIG. 1 in more detail;

FIG. 3 shows a sensing configuration with associated processing; and

DESCRIPTION OF THE PREFERRED EMBODIMENTS

Figure 1:
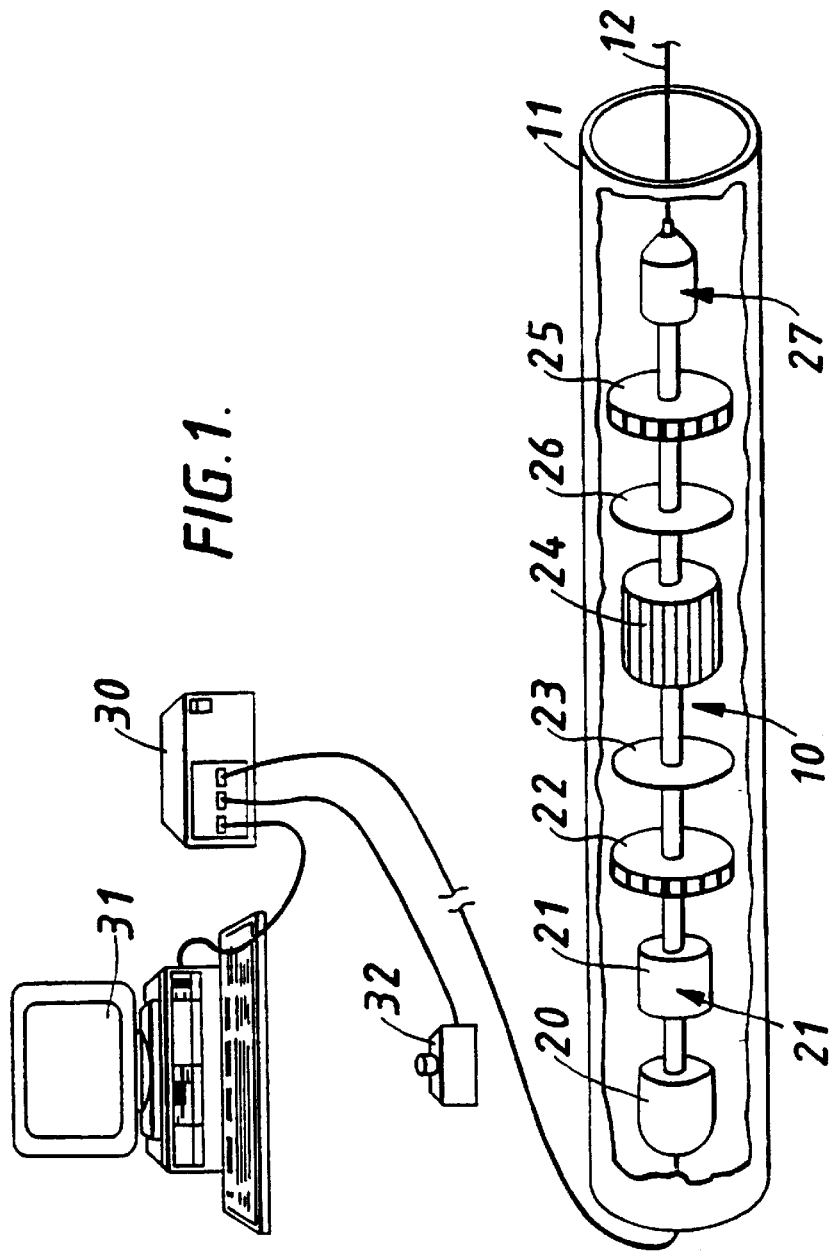
FIG. 1 shows an embodiment of the pipeline vehicle of the present invention.

The pipeline inspection arrangement of FIG. 1 comprises a towed vehicle 10 shown within pipe 11 which can be towed by a winch (not shown) via cable 12 to allow testing of a pipe through which it passes. The towed vehicle comprises several linked devices. These include a power unit 20 and master processor module 21 and a master sensor ring 22. A coil 24 generates a remote field eddy current which is detected via sensor ring 22. The coil is separated from the sensor ring 22 by means of separator 23 to attenuate any directly transmitted field between the coil 24 and sensor 22. A slave ring 25 is also provided separated from the coil 24 by attenuating separator 26. The sensor ring 25 is connected to slave processor module 27. A base station 30 provides the link between the vehicle 10 and a computer 31 so as to initiate testing and to receive resulting information. A distance encoder 32 is provided to generate distance information as the vehicle travels through the pipeline. The distance encoder can conveniently be mounted on the cable wheel (not shown) associated with the winch so that as the vehicle is towed the distance travelled is continuously updated back to the base station 30.

The arrangement is configured to induce eddy currents into the wall of the pipeline due to the a.c. field generated by coil 24. We have determined that such eddy currents can be used in both ferrous and non-ferrous pipelines (i.e. magnetic and non-magnetic) and with a smooth pipe wall a uniform field decaying with distance is provided. When non uniformity in the surface is present due to pitting, cracks, etc., then changes in the detected eddy currents field occurs and these are detected via sensor arrays 22 and 25. By utilising two sensor array sets the ability to pinpoint the defect point is enhanced. In addition each sensor array have typically twenty-four sensors in each so that in total 48 amplitude sensing and 48 phase sensing measurements can be made covering the periphery of the pipe. We have determined that by taking phase measurements in addition to the amplitude measurements it is possible to discriminate between internal and external pipe wall defects. The information to and from the base station can be passed on 48 analogue and 48 digital channels.

The arrangement described is capable of operating within small pipes of 4" diameter or less and has capability of coping with bends having a radius 1.5 times the diameter of the pipeline.

The system can typically provide a 6 mm scan interval with a winch speed of about 6 meters per minute. An x and y accelerometer is incorporated within the vehicle to allow orientation information to be sent to the computer as the vehicle may partially rotate during its travel through the pipeline. The towing range can be several hundred meters so providing a very useful and cost effective inspection mechanism.

The information passed to computer 31 via base station 30 allows a number of parameters to be determined from the detected information. This can give a 'real-time' display of:

1. amplitude and phase
2. azimuth 0–360°
3. velocity

In addition the defects can be calculated to include the size and position of defects using the computer.

The vehicle of FIG. 1 will have electronic control, power and data transmission requirements which are shown in more detail in FIG. 2.

The vehicle power requirements are received on line 35 and pass to power unit 20. The input can be 110V a.c. supply and the power unit output will be 150V d.c. for the coil drive requirements using line 33. Low voltage d.c. will be available for the electronics circuits within the vehicle (e.g. ±5V). Communication to and from the vehicle and the base station will be via connection 30a. A suitable communication protocol will be employed (e.g. RS 232).

The master processor 21 will be microprocessor controlled and include data links between the master sensor assembly 22 and the slave processor to ensure synchronism as well as control 38 to the coil drive. Serial data passes between master processor 21 and sensor 22 via line 37. There is also passage of data between slave processor 27 and sensor 25 via line 34. Rather than incorporating all the processing requirements within the slave and master processors 27 and 21, it is possible to provide signal conditioning and processing within the sensor assembly as shown in FIG. 3 for the master sensors 22, where two sensor coils 22a and 22b of the sensor array 22 are shown. Here dedicated acquisition hardware (signal conditioning 22d,c and microcontroller 22f) give improved noise performance and reduced processing load to the processor in the master pack 21, and allow increased front-end processing.

Timing of data sampling will be controlled by the phase reference input. Sample rate will be dependent upon the excitation frequency selected.

The microcontroller will be implemented using an 8 bit mIcrocontroller with minimum port capability. The serial data interface will adopt a standard protocol.

Channels will be paired as shown, each microprocessor 22f supporting two sensor channels 22a, 22b with associated signal conditioning 22d, 22c.

Returning to FIG. 2, the single drive coil 24 provides field excitation and the sensors are maintained in close proximity to the pipe wall with x and y orientation sensors in each sensor assembly 22, 25 to compensate for rotation within the pipe and skew between the two sensor assemblies. Prior to operation, the vehicle identification is read and data is loaded into a calibration file within the computer 31.

Vehicle configuration is then set up via the computer to give the number of channels and sensor address requirements.

In addition the coil current is set to meet operational requirements.

Finally the coil excitation frequency is set. This may be within the range of 20 Hz to 1 KHZ and selected dependent on the pipeline material under investigation as both ferrous and non-ferrous pipelines are to be tested. In operation the vehicle is towed through the pipe and as it does so the distance encoder 32 of FIG. 1 will produce data or distance travelled.

Figure 4:
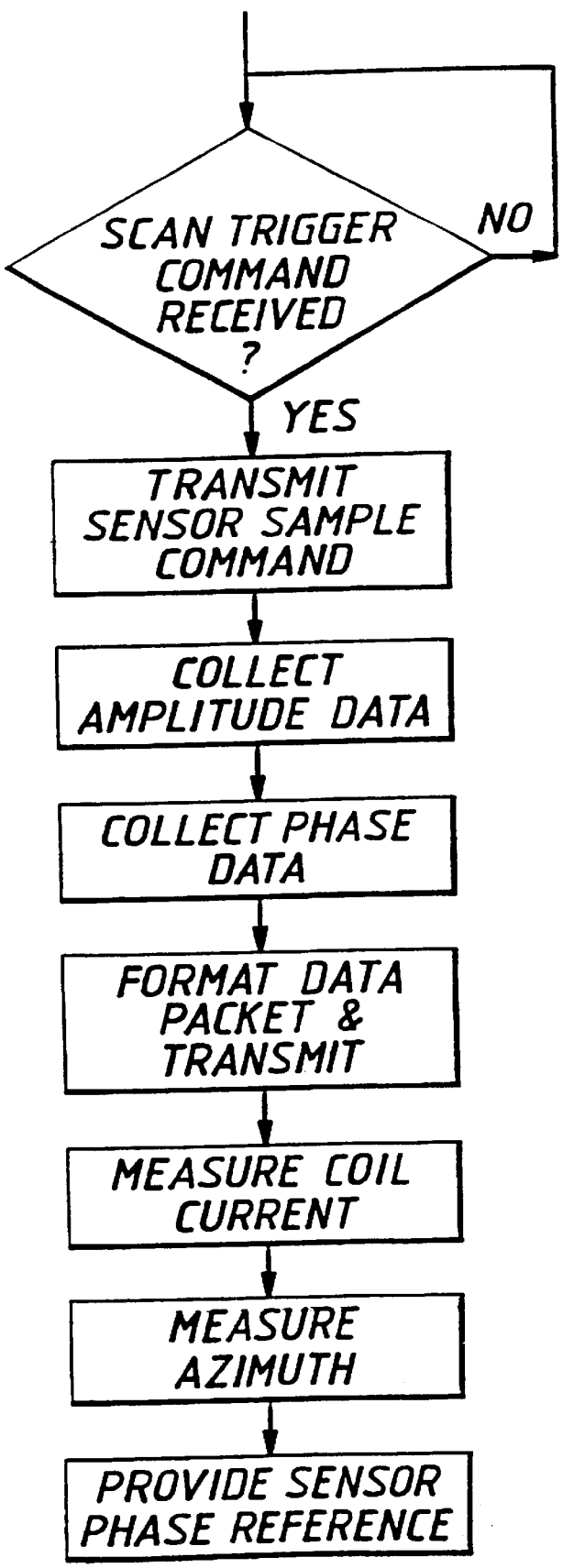
FIG. 4 shows a flow chart associated with system operation.

To determine defects in the pipeline, a data scan command is sent from the computer and received via the base station in the vehicle master controller. This information is then repeated to the slave controller by the master. Scanning to the channels is then effected. The slave sends the data to the master in packet format and the master receives data also from the master sensors. The master assembles the data including amplitude and phase information and orientation data from both sensor rings and sends this to the host computer for display and processing. A flow chart of typical system operation is shown in FIG. 4. In addition the master controller synchronises the slave and generates tied drive coil excitation signal. Compensating time delays can be incorporated to ensure synchronisation between master and slave.

What is claimed is:

1. A method of testing a pipeline using a pipeline inspection device, comprising the steps of:
    loading a composition information of a pipeline to be tested into a processing unit;
    selecting a coil excitation frequency based on the composition information;
    generating an eddy current field in a transmitter coil disposed in the pipeline inspection device;
    detecting an induced eddy current field in a wall of the pipeline at two longitudinally spaced locations, on each side of the transmitter coil; and
    updating periodically an information of the induced eddy current field as the device travels along the pipeline to allow faults in the pipeline to be determined.

2. A method as claimed in claim 1 wherein the frequency is selected within the range 20 Hz to 1 kHz.

3. A method as claimed in claim 1 including attenuating any signal received by the detecting step other than received via the pipeline wall.

4. A method as claimed in claim 1, wherein the detecting step includes detecting the amplitude and the phase of the eddy current to discriminate between internal and external pipe wall defects.

5. A method as claimed in claim 1 including the steps of towing the device along the pipeline, determining the distance travelled and determining the orientation of the detector position in the pipeline as the device travels through the pipeline.

6. A method as claimed in claim 1 including the step of determining the dimensions of a fault in the pipeline from detected information.

7. A method as claimed in claim 1 wherein the device comprises a towed vehicle capable of passing trough bends in the pipeline and the steps include towing the vehicle through the pipeline, sensing a first azimuth value at a location of a first receiver and sensing a second azimuth value at a location of a second receiver to provide orientation information to compensate for vehicle rotation within the pipeline and any skew between the first and second receivers as the vehicle travels through the pipeline.

8. A method as claimed in claim 1, further comprising the steps of:
    sending a scanning command from a data processing unit to the pipeline inspection device;
    collecting an amplitude data in response to said scanning command;
    collecting a phase data in response to said scanning command;
    formatting the amplitude and phase data into a packet and transmitting the packet to said data processing unit; and
    detecting an azimuth information to provide orientation information to compensate for a vehicle rotation within the pipeline.

9. A pipeline inspection device for traveling through a pipeline, comprising:
    a generator unit having a transmitter coil configured to induce an eddy current field into a wall of the pipeline;

a detector unit comprising first and second receivers spaced longitudinally on each side of the transmitter coil and configured to detect periodically, as the device travels through the pipeline, a resultant field which is derived from the eddy current field propagated through the wall of the pipeline, at two longitudinally spaced locations on the pipeline; and a data processing unit configured to select an excitation frequency for the transmitter coil dependent on a pipeline composition information of the pipeline to be tested, wherein the pipeline composition information is loaded into the data processing unit before operating the pipeline inspection device.

10. The pipeline inspection device of claim 9, wherein the data processing unit is configured to select a frequency within a range of 20 Hz to 1 kHz.

11. The pipeline inspection device of claim 9, further comprising first and second separators disposed between the transmitter coil, wherein the transmitter coil is a single drive coil, and the first and second receivers, said separators being configured to attenuate any signal reaching the first and second receivers other than through the pipeline wall.

12. The pipeline inspection device of claim 11, comprising:

a master processor connected to the first receiver and the transmitter coil; and a slave processor connected to the second receiver and the master processor, wherein the master processor is configured to control said first and second receivers and the transmitter coil, and to provide a synchronizing information to the second receiver via the slave processor.

13. The pipeline inspection device of claim 9, wherein the data processing unit is configured to determine both an amplitude and a phase of the resultant field and to discriminate between internal and external pipe wall defects, based on the amplitude and the phase of the resultant field.

14. The pipeline inspection device of claim 9, further comprising:

a cable configured to tow the pipeline inspection device through the pipeline;

a distance encoder configured to determine distance information of the pipeline inspection device; and a master sensor array ring configured to determine an azimuth orientation of the pipeline inspection device as the device travels through the pipeline.

15. The pipeline inspection device of claim 13, wherein the data processing unit is configured to display the detected amplitude, phase, azimuth and a velocity as the pipeline inspection device travels along the pipeline.

16. The pipeline inspection device of claim 9, comprising a master processor module configured to generate data packets that are transmitted to the data analyzing unit for evaluation.

17. The pipeline inspection device of claim 9, wherein the data analyzing unit is configured to determine each dimension of a faulty portion of the pipeline.

18. The pipeline inspection device of claim 14, wherein the master sensor array ring comprises a plurality of sensor coils, each sensor coil being connected through a signal conditioning module to a microprocessor, said microprocessor being configured to receive a phase reference signal for data sampling timing.

19. The pipeline inspection device of claim 9, wherein each of the first and second receiver comprises a ring of sensors spaced around a periphery of the receivers.

20. The pipeline inspection device of claim 9, wherein the pipeline inspection device further comprises:

a towed vehicle configured to pass through bends in the pipeline;

a first azimuth sensor located on the first receiver; and a second azimuth sensor located on the second receiver, wherein the first and second azimuth sensors are configured to provide orientation information to compensate for the towed vehicle rotation within the pipeline and any skew between the first and second receivers.

* * * * *